US012484987B2

(12) United States Patent
Shang et al.

(10) Patent No.: US 12,484,987 B2
(45) Date of Patent: Dec. 2, 2025

(54) BARRIER CARTRIDGE AND A BARRIER ASSEMBLY

(71) Applicant: Precision Robotics Limited, London (GB)

(72) Inventors: Jianzhong Shang, Dartford (GB); Tamas Csaba Hernadi, London (GB); Joshua Arieh Shenker, Borehamwood (GB)

(73) Assignee: Precision Robotics Limited, London (GB)

( * ) Notice: Subject to any disclaimer, the term of this patent is extended or adjusted under 35 U.S.C. 154(b) by 478 days.

(21) Appl. No.: 18/003,961

(22) PCT Filed: Jun. 25, 2021

(86) PCT No.: PCT/GB2021/051624
§ 371 (c)(1),
(2) Date: Dec. 30, 2022

(87) PCT Pub. No.: WO2022/003328
PCT Pub. Date: Jan. 6, 2022

(65) Prior Publication Data

US 2023/0255712 A1 Aug. 17, 2023

(30) Foreign Application Priority Data

Jul. 2, 2020 (GB) ...................................... 2010152

(51) Int. Cl.
*A61B 46/10* (2016.01)
*A61B 34/30* (2016.01)

(52) U.S. Cl.
CPC .............. *A61B 46/10* (2016.02); *A61B 34/30* (2016.02)

(58) Field of Classification Search
CPC ................................ A61B 34/30; A61B 46/10
See application file for complete search history.

(56) References Cited

U.S. PATENT DOCUMENTS

| | | | |
|---|---|---|---|
| 11,304,765 B2 | 4/2022 | Chaplin et al. | |
| 11,839,438 B2 | 12/2023 | Marshall et al. | |
| 2020/0297434 A1 | 9/2020 | Bencteux et al. | |

FOREIGN PATENT DOCUMENTS

| | | | |
|---|---|---|---|
| CN | 110251236 A * | 9/2019 | ............. A61B 34/70 |
| GB | 2586998 A | 3/2021 | |

(Continued)

OTHER PUBLICATIONS

International Search Report from PCT International Application No. PCT/GB2021/051624, dated Oct. 11, 2021.

*Primary Examiner* — Scott Luan
(74) *Attorney, Agent, or Firm* — Budzyn IP Law, LLC

(57) ABSTRACT

A barrier cartridge for providing a sterility barrier between movable interfaces comprising a barrier with first and second ends; a barrier receiving portion, adapted to receive the barrier, and comprising first second ends spaced apart from one another, first and second sides spaced apart from one another and extending between the first and second ends, wherein the barrier is attachable to the barrier receiving portion such that it extends between the first and second sides of the barrier receiving portion and is movable between the first and second ends of the barrier receiving portion; first and second flex cards each operatively connected to both the respective end of the barrier and the respective end of the barrier receiving portion and extendible between the first and second sides of the barrier receiving portion.

16 Claims, 9 Drawing Sheets

(56) References Cited

FOREIGN PATENT DOCUMENTS

| | | | | |
|---|---|---|---|---|
| KR | 20180138202 | A | 12/2018 | |
| WO | 2016081286 | A1 | 5/2016 | |
| WO | WO-2018020252 | A2 * | 2/2018 | ............. A61B 34/30 |

* cited by examiner

BARRIER CARTRIDGE AND A BARRIER ASSEMBLY

CROSS-REFERENCE TO RELATED APPLICATIONS

This Application is a National Stage Application under 35 U.S.C. § 371 of PCT Application No. PCT/GB2021/051624, filed Jun. 25, 2021, which claims priority to UK Patent Application No. 2010152.3, filed Jul. 2, 2020, the entire contents of which are incorporated by reference herein.

BACKGROUND OF THE INVENTION

1. Field of the Invention

This invention relates to a barrier assembly for providing a sterility barrier between sterile and non-sterile surfaces and a barrier cartridge, which forms part of the barrier assembly, for providing a sterility barrier between movable interfaces. The invention may have particular application in the field of surgical robotics to provide a sterility barrier between sterile and non-sterile instruments, although the invention is not limited to such applications.

2. Description of the Related Art

Robotic systems are increasingly being used to carry out surgical procedures, particularly minimally invasive surgeries in which miniaturised surgical robotic instruments may be remotely controlled by a surgeon. However, surgical robots raise a variety of unique challenges, one of which is how to ensure the sterility of any components that may contact the patient.

From here in, within the context of an operating theatre, sterility may be considered relative to the patient being operated on. Therefore, any surface that may contact the patient should be sterile prior to use and may still be considered as being sterile after coming into contact with the patient or any other sterile surface. However, once a sterile surface has contacted a non-sterile surface, other than the patient, that surface is considered as being contaminated and is therefore non-sterile.

One approach to ensure the sterility of components of a surgical robot that may contact the patient is to provide reusable devices that are sterilised between each use. However, it is difficult to design such a device that is intricate enough to perform its required function but is also robust enough to withstand multiple sterilization cycles.

Another approach is to provide disposable devices that require only a single sterilization, typically by the manufacturer. However, this is only practical for low-cost parts as it would not be sustainable to replace an entire surgical robotic system after each surgery.

Therefore, known surgical robots comprise a combination of single-use and reusable components. The single-use components may be those that directly contact the patient and are replaced after each use to ensure their sterility at the start of each procedure. The single-use components may also be producible in a cost effective and sustainable way. The reusable components may be those that do not come into direct contact with the patient and which are more expensive to manufacture such as motorised components for example.

However, a challenge with combining sterile single-use components with non-sterile reusable components is that the non-sterile surfaces of the reusable components may contact and contaminate surfaces of the single-use components, hence compromising their sterility. The contamination may then be transmitted to the patient.

SUMMARY OF THE INVENTION

A solution to this challenge is to cover the non-sterile reusable components of the surgical robot with a sterile drape or bag so that the sterile components and the patient are not contaminated. However, such a covering is not always effective, particularly for surgical robots in which the sterile and non-sterile components are required to interact with one another in order for a sterile surgical instrument to be able to carry out its required function. Further, known surgical robots may require a sterile component to move relative to the non-sterile components while ensuring that its sterility is not compromised. Therefore, a sterility barrier is required that facilitates movement of sterile and non-sterile components while maintaining a sterility barrier between those components.

According to a first aspect of the invention there is provided a barrier cartridge for providing a sterility barrier between movable interfaces comprising: a barrier comprising a first end and a second end; a barrier receiving portion, adapted to receive the barrier, and comprising a first end and a second end spaced apart from one another, a first side and a second side spaced apart from one another and extending between the first and second ends, wherein the barrier is attachable to the barrier receiving portion such that it extends between the first side and the second side of the barrier receiving portion and is movable between the first end and the second end of the barrier receiving portion; a first flex card operatively connected to both the first end of the barrier and the first end of the barrier receiving portion and extendible between the first and second sides of the barrier receiving portion; and a second flex card operatively connected to both the second end of the barrier and the second end of the barrier receiving portion and extendible between the first side and the second side of the barrier receiving portion.

In use, the barrier may be attachable to a first movable interface and a second movable interface wherein the first movable interface forms part of a non-sterile component, the second movable interface forms part of a sterile component and the barrier acts as a sterility barrier between the first and second movable interfaces.

The barrier extends between the first and second sides of the barrier receiving portion of the barrier cartridge and, further, is movable between the first and second ends of the barrier receiving portion. The first and second flex cards also extend between the first and second sides of the barrier receiving portion, with the first flex card operatively connected to both the first end of the barrier and the first end of the barrier receiving portion while the second flex card is operatively connected to both the second end of the barrier and the second end of the barrier receiving portion. A sterility barrier is thereby formed across the entire barrier receiving portion by a combination of the barrier, the first flex card and the second flex card.

Hence, by means of the invention, a barrier cartridge is provided that may act as a sterility barrier between a first movable interface and a second movable interface while allowing the interfaces to move between first and second ends of the barrier receiving portion.

The first flex card may comprise a barrier end attachable to the first end of the barrier and a cartridge end opposite to the barrier end. The cartridge end may be spaced apart from the barrier end such that, when the barrier is positioned at the second end of the barrier receiving portion, the first flex card extends from the first end of the barrier to at least the first end of the barrier receiving portion. This allows the first flex card to be operatively connected to both the first end of the barrier and the first end of the barrier receiving portion, even when the barrier is as far away as possible from the first end of the barrier receiving portion.

The second flex card may similarly comprise a barrier end attachable to the second end of the barrier and a cartridge end opposite to the barrier end. The cartridge end may be spaced apart from the barrier end such that, when the barrier is positioned at the first end of the barrier receiving portion, the second flex card extends from the second end of the barrier to at least the second end of the barrier receiving portion. This allows the second flex card to be operatively connected to both the second end of the barrier and the second end of the barrier receiving portion, even when the barrier is as far away as possible from the first end of the barrier receiving portion.

Each flex card may be operatively connected to the barrier and the respective end of the barrier receiving portion as the barrier moves between the first and second ends of the barrier receiving portion. For example, each flex card may be slidably received by the respective end of the barrier receiving portion, or the cartridge end of each flex card may be attachable to the respective end of the barrier receiving portion.

The barrier cartridge, the barrier, the first flex card and the second flex card may each comprise a first face and a second face. In use the first faces may be exposed to the non-sterile region and the second faces may be exposed to the sterile region. In order to ensure that the sterile region avoids contamination and remains sterile, the second faces must not be exposed to the non-sterile region. In embodiments of the invention, the barrier cartridge may further comprise a flex card sterility mechanism.

In some embodiments of the invention each flex card may be slidably receivable by the respective end of the barrier receiving portion. At any given time when the invention is in use, each flex card may thereby comprise a portion that is positioned internally of the barrier receiving portion (i.e. extending between the barrier and the respective end of the barrier receiving portion) and a portion that is positioned externally of the barrier receiving portion (i.e. extending outwardly from the respective end of the barrier receiving portion). For the portion of each flex card that is positioned internally of the barrier receiving portion, the second (sterile) face may be protected from the non-sterile region by the barrier and barrier cartridge that surround it. However, the portion of each flex card that is positioned externally of the barrier receiving portion may extend loosely from the barrier cartridge and be exposed to potential contamination by contact with a non-sterile surface.

Therefore, in embodiments of the invention, the flex card sterility mechanism may comprise a first pocket operatively connectable to the first end of the barrier receiving portion and adapted to receive a portion of the first flex card that is positioned externally of the barrier receiving portion and a second pocket operatively connectable to the second end of the barrier receiving portion and adapted to receive a portion of the second flex card that is positioned externally of the barrier receiving portion.

In such embodiments of the invention, the portion of each flex card that is positioned externally of the barrier receiving portion is concealingly received by a respective pocket in order to protect particularly the second face of the flex card so that it remains sterile.

Each pocket may comprise a first internal wall and a second internal wall spaced apart from the first internal wall. When the portion of the respective flex card that is positioned externally of the barrier receiving portion is received by the pocket, the first face of the flex card may contact the first internal wall only and the second face may contact the second internal wall only. This means that there is no contact between the second (sterile) face of the flex card and the non-sterile first internal wall.

In other embodiments of the invention the flex card sterility mechanism may comprise a first anchor wherein the first flex card is attachable to the first anchor such that the first flex card extends from the first end of the barrier to the first anchor via the first end of the barrier receiving portion, and a second anchor wherein the second flex card is attachable to the second anchor such that the second flex card extends from the second end of the barrier to the second anchor via the second end of the barrier receiving portion.

In such embodiments of the invention the barrier end of each flex card may be attachable to the respective end of the barrier while the cartridge end of each flex card is attachable to the respective anchor. A portion of each flex card that is positioned internally of the barrier receiving portion may extend between the barrier and the respective end of the barrier receiving portion while a portion of each flex card that is positioned externally of the barrier receiving portion may extend from the respective end of the barrier receiving portion to the respective anchor.

Each anchor may be positioned, on the barrier cartridge, proximate to the respective end of the barrier receiving portion such that the portion of the respective flex card that is positioned externally of the barrier receiving portion is caused to roll or fold back on itself in order to attach to the anchor.

Further, each anchor may be positioned, on the barrier cartridge, such that the first (non-sterile in use) face of the flex card forms the outer face of the folded/rolled portion of the respective flex card that is positioned externally of the barrier receiving portion and the second (sterile) face of the flex card forms the inner face of the folded/rolled portion of the respective flex card that is positioned externally of the barrier receiving portion. The portion of the second face of each flex card that is positioned externally of the barrier receiving portion is therefore substantially concealed within the fold/roll and protected from contacting a non-sterile surface.

In different embodiments of the invention each flex card is attachable to the respective end of the barrier receiving portion and the flex card sterility mechanism comprises at least one fold-line extending across each flex card substantially perpendicular to the first and second sides of the barrier receiving portion when in use such that each flex card is corrugated and thereby extendible or contractable as the barrier moves between the first end and the second end of the barrier receiving portion.

In such embodiments of the invention each flex card is entirely positioned internally of the barrier receiving portion and extends between the barrier and the respective end of the barrier receiving portion only. Therefore there is no portion of either flex card that is positioned externally of the barrier receiving portion and hence no portion of the second (sterile) face of either flex card that becomes exposed to a non-sterile region where it may come into contact with a non-sterile surface.

In order for each flex card to remain positioned internally of the barrier receiving portion while the barrier moves between the first and second ends of the barrier receiving portion, each flex card is corrugated. Here corrugated means that each flex card is adapted to fold along the at least one fold-line extending across each flex card substantially perpendicular to the first and second sides of the barrier receiving portion and/or substantially parallel to the barrier and cartridge ends of the flex card.

In use, when the barrier is positioned towards the second end of the barrier receiving portion, the first flex card is substantially flat in order to extend the relatively large gap between the barrier and the first end of the barrier receiving portion. Conversely, the second flex card is substantially folded against itself in order that the barrier and cartridge ends of the second flex card can be positioned relatively proximal to one another as the second flex card is only required to extend the relatively small gap between the barrier and the second end of the barrier receiving portion. As the barrier moves from the second end to the first end of the barrier receiving portion the first flex card may gradually fold against itself while the second flex card may gradually flatten.

In some embodiments of the invention each flex card may comprise a single fold-line only positioned approximately at the middle of the flex card. In such embodiments of the invention, the central portion of the flex card may project away from the barrier receiving portion. In other embodiments of the invention each flex card may comprise a plurality of fold-lines distributed evenly between the barrier and cartridge ends of the flex card. In such embodiments of the invention the flex card may expand and contract in an accordion-like fashion as the barrier moves between the first and second ends of the barrier receiving portion.

In embodiments of the invention the barrier receiving portion comprises: a first channel extending along the first side and configured to slidably receive a first side of each flex card, and a second channel extending along the second side and configured to slidably receive a second side of each flex card.

In such embodiments of the invention each flex card may extend between the first and second sides of the barrier receiving portion such that the first side of the flex card is slidably received in the first channel and the second side of the flex card is slidably received in the second channel. This may ensure that there are no gaps between the sides of the flex cards and the sides of the barrier receiving portion through which contaminants may be able to pass from a non-sterile region (comprising non-sterile components, for example) to a sterile region (comprising sterile components and a patient, for example). Further, the first and second channels may support the flex cards and ensure they remain aligned with the barrier across the barrier receiving portion.

In embodiments of the invention the barrier receiving portion may also comprise one or more further channels to provide further functionality.

In embodiments of the invention the barrier comprises a first cartridge interface slidably engageable with the first channel, and a second cartridge interface slidably engageable with the second channel.

In such embodiments of the invention the barrier may be positioned such that the first cartridge interface is slidably engaged with the first channel extending along the first side of the barrier receiving portion, the barrier extends from the first side to the second side of the barrier receiving portion and the second cartridge interface is slidably engaged with the second channel extending along the second side of the barrier receiving portion. The barrier may thereby be slidably engaged with the barrier receiving portion. Further, the first and second cartridge interfaces may be adapted such that there are no gaps between the barrier and the sides of the barrier receiving portion through which contaminants may be able to pass from a non-sterile region to a sterile region.

Accordingly, the barrier and each flex card may be adapted to extend from the first channel to the second channel of the barrier receiving portion such that there are no gaps through which contaminants may be able to pass from a non-sterile region to a sterile region.

However, in embodiments of the invention, the barrier receiving portion may comprise one or more further channels extending along its sides. For example, a side of each of the first and second flex cards may be slidably engageable with one channel while a respective side of the barrier is slidably engageable with a different channel.

In embodiments of the invention the barrier comprises a first face, a second face spaced apart from the first face and a translator mechanism extending between the first face and the second face, the translator mechanism comprising a plurality of translators wherein each translator comprises: a body positioned between the first face and the second face, an actuation portion accessible through a first aperture in the first face and moveable within the first aperture, and a translation portion accessible through a second aperture in the second face and moveable within the second aperture, wherein the actuation portion is operatively connected to the body and to the translation portion such that movement of the actuation portion causes movement of the body and the translation portion, and the body maintains a sterility barrier between the first and second apertures irrespective of its position.

In use, the first face may be attachable to a first movable interface and the second face may be attachable a second movable interface wherein the first movable interface forms part of a non-sterile component, the second movable interface forms part of a sterile component and the barrier acts as a sterility barrier between the first and second movable interfaces.

In such embodiments of the invention, the first movable interface may comprise a plurality of actuators, each engageable with a respective actuation portion and configured to actuate that actuation portion within the respective first aperture. Movement of each actuation portion may cause equivalent movement of the body and translation portion of the translator. The second movable interface may also comprise a plurality of actuators, each engageable with a respective translation portion and configured to be actuated by the translation portion moving within the respective second aperture. Accordingly, each translator may translate movement of an actuator forming part of the first movable interface to movement of an actuator forming part of the second movable interface.

Further, the body of each translator maintains a barrier between the first and second apertures irrespective of its position and therefore acts as a sterility barrier between first (non-sterile) movable interface and the second (sterile) movable interface.

Hence, by means of the invention, a sterility barrier is provided that allows a non-sterile moving part to interact with a sterile moving part without compromising the sterility of the sterile moving part.

In embodiments of the invention the first and second apertures of the barrier are first and second linear slots respectively, whereby the respective actuation and translation portions are movable linearly within the first and second linear slots respectively.

In such embodiments of the invention, each actuator forming part of the first movable interface may be movable linearly and each of the first slots may be configured to align with the linear range of movement of the respective actuator belonging to the first movable interface. Similarly, each actuator forming part of the second movable interface may also be movable linearly and each of the second slots may be configured to align with the linear range of movement of the respective actuator belonging to the second movable interface.

Each slot may be substantially rectangular in shape and defined as having a width and a length. The width of each slot may be configured to prevent movement of the respective actuation or translation portion in a direction parallel to the width. Whereas, the length of each slot may be configured such that the respective actuation or translation portion is movable linearly along the length. Hence each actuation or translation portion is movable only linearly within the respective slot. Respective first and second slots may have widths and lengths that are substantially the same as one another or may have widths and lengths that are different to one another.

In order to maintain a barrier between the first and second slots, the body may have a width that is at least the width of first and second slots. Further the body may extend a first length either side of the translation portion such that the body prevents objects passing through the first slot, irrespective of the position of the translation portion within the first slot. The first length may be at least the length of the first slot. Similarly the body may extend a second length either side of the actuation portion such that the body prevents objects passing through the second slot, irrespective of the position of the actuation portion within the second slot. The second length may be at least the length of the second slot.

In embodiments of the invention the first face of the barrier is removably engageable with a motor module comprising a plurality of motor actuators, and the actuation portion of each translator is engageable with a respective one of the motor actuators.

In such embodiments of the invention, the first movable interface forms part of the motor module and the plurality of actuators forming part of the first movable interface are the plurality of motor actuators.

The motor module may comprise one or more motors configured to drive movement of the motor actuators. The motor module may be a re-usable part due to the expense that may be associated with producing the motors and related electrical components. Hence, the motor may be non-sterile in use.

In embodiments of the invention the second face of the barrier is engageable with a driver module comprising a plurality of drive actuators, and the translation portion of each translator is engageable with a respective one of the drive actuators.

In such embodiments of the invention, the second movable interface forms part of the driver module and the plurality of actuators forming part of the second movable interface are the plurality of drive actuators.

The driver module may be passive and may comprise no electrical components. Therefore, the driver may be cost-effectively producible as a single-use part. Hence the driver module may be sterile in use.

Each drive actuator may be actuated by a respective translator via the actuation portion, the translator in turn being actuated by a respective motor actuator via the translation portion. Accordingly the barrier may translate actuations provided by the motor module to actuation of the driver module while providing a sterility barrier between them.

According to a second aspect of the invention there is provided a barrier assembly for providing a sterility barrier between sterile and non-sterile surfaces wherein the barrier assembly is mountable to a platform for a robotic surgical platform and comprises: a bracket comprising at least one barrier cartridge according to the first aspect of the invention; and a first drape removably attachable to the bracket.

By means of the invention a sterility barrier is provided that may prevent contamination of sterile single-use components of a surgical robot by providing a physical barrier between those components and non-sterile reusable components of the surgical robot. Particularly, the barrier cartridge may provide a sterility barrier between movable interfaces such as a non-sterile motor module interface and a sterile driver module interface. Further, the first drape may flexibly cover a plurality of non-sterile components of the surgical robot such as the platform for mounting the surgical instruments to one or more motor modules and any other suitable components of the surgical robot that may be non-sterile in use. As well as protecting the sterile components from contact with the non-sterile components of the surgical robot, the drape may also prevent medical staff from contaminating their sterile protective clothing (e.g. gloves and gowns) by accidentally contacting non-sterile surface of the surgical robot.

In embodiments of the invention the bracket may comprise any suitable number of barrier cartridges according to the first aspect of the invention and hence the surgical robot may comprise any number of surgical instruments.

In some embodiments of the invention the bracket comprises two barrier cartridges according to the first aspect of the invention.

In such embodiments of the invention, the surgical robot may comprise two surgical instruments, each actuated by its own driver module and motor module. Each barrier cartridge may therefore act as a sterility barrier between the respective driver module and motor module.

For example, in use, a surgeon may control a different surgical instrument with each hand and thereby control two surgical instruments simultaneously.

In embodiments of the invention the barrier assembly further comprises a port removably attachable to the bracket.

In such embodiments of the invention the port may support surgical instruments and facilitate their insertion into the patient via a natural orifice or incision.

In embodiments of the invention a first face of the bracket is mountable, via the platform, to a manipulator arm configured to movably mount the bracket to a surface and selectively provide the bracket with six degrees of freedom of movement relative to the surface. The manipulator arm may allow the surgical instruments to be positioned relative to the patient, as required for the surgical operation.

In such embodiments of the invention the manipulator arm may be reusable and non-sterile in use. The first drape may flexibly cover the manipulator arm, irrespective of the position it is configured to. Therefore the first drape may provide a sterility barrier between the manipulator arm and any of the various sterile surface in the operating theatre, such as the surgical instruments, the protective clothing of medical staff and the patient.

In embodiments of the invention the barrier assembly further comprises a second drape removably attachable to the bracket wherein the first drape is operatively connectable to a first face of the bracket and the second drape is operatively connectable to a second face of the bracket.

In use, the first face of the bracket may be exposed to a non-sterile region (comprising non-sterile surfaces) while the second face of the bracket is exposed only to a sterile region (comprising sterile surfaces). The outer face of the first drape may therefore be considered as non-sterile while the outer face of the second drape may remain sterile. Further, a second sterile region may also be provided between the first and second drapes (between the inner face of each drape).

In such embodiments of the invention, the first and second flex cards forming part of the, or each, barrier cartridge may be configured such that a portion of each flex card which is positioned externally of the barrier receiving portion is also positioned between the first and second drapes. This may protect the second (sterile) face of each flex card from being contaminated and may also protect the outer face of the second drape from being contaminated by contact with the first (non-sterile in use) face of any of the flex cards.

The second drape may also provide a level of redundancy to the sterility barrier so that the sterility of sterile surfaces is not compromised if the first drape is damaged.

In embodiments of the invention the drape or each drape is sleeve-shaped and comprises a first end removably attachable to the bracket and a second end removably attachable to the manipulator arm such that the first face of the bracket is covered by the drape or both drapes.

In such embodiments of the invention the, or each, drape may encase non-sterile components of the surgical robot (such as the platform, motor modules and manipulator arm) in order to ensure that they do not contact sterile surfaces in the operating theatre.

According to a third aspect of the invention there is provided a barrier according to that described as forming part of the first aspect of the invention.

BRIEF DESCRIPTION OF THE DRAWINGS

The invention will now be described by way of example only with reference to the accompanying drawings in which.

DETAILED DESCRIPTION OF THE EMBODIMENTS

Figure 1:
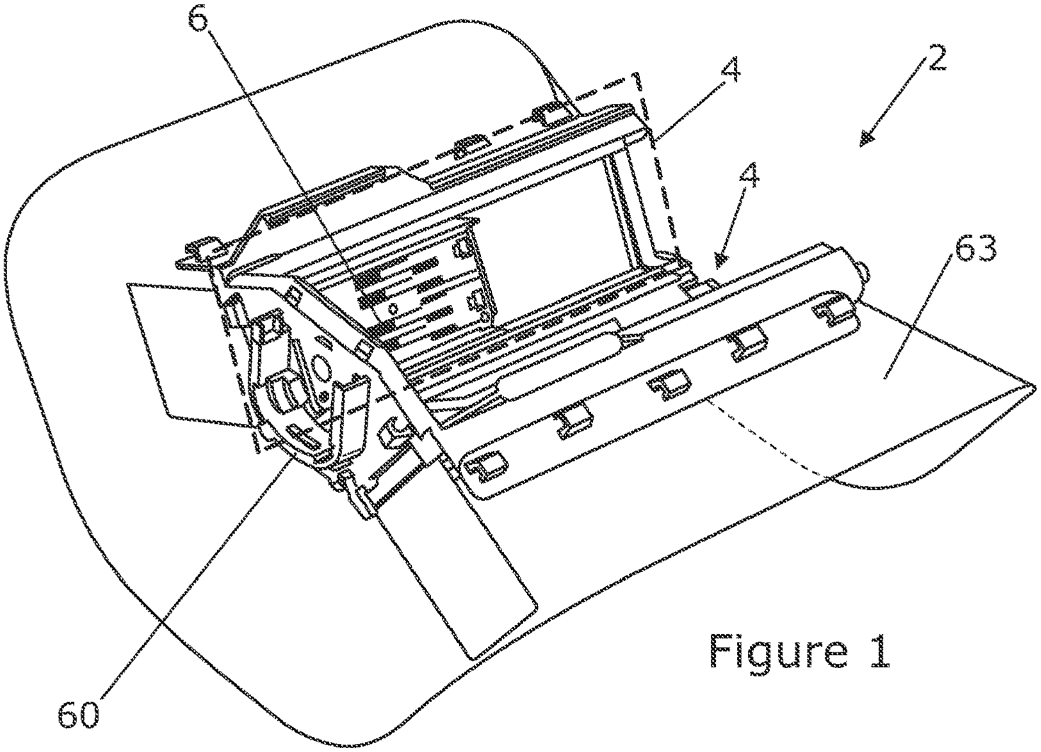
FIG. 1 is a schematic representation of a barrier assembly according to an embodiment of the second aspect of the invention.

Referring initially to FIG. 1, a barrier assembly according to the second aspect of the invention is designated generally by the reference numeral 2. The barrier assembly comprises two barrier cartridges 4 according to the first aspect of the invention, which in turn each comprise a barrier 6 according to the third aspect of the invention. The barrier assembly 2 further comprises a bracket 60 and a drape 63 removably attachable to the bracket 60.

Figure 2:
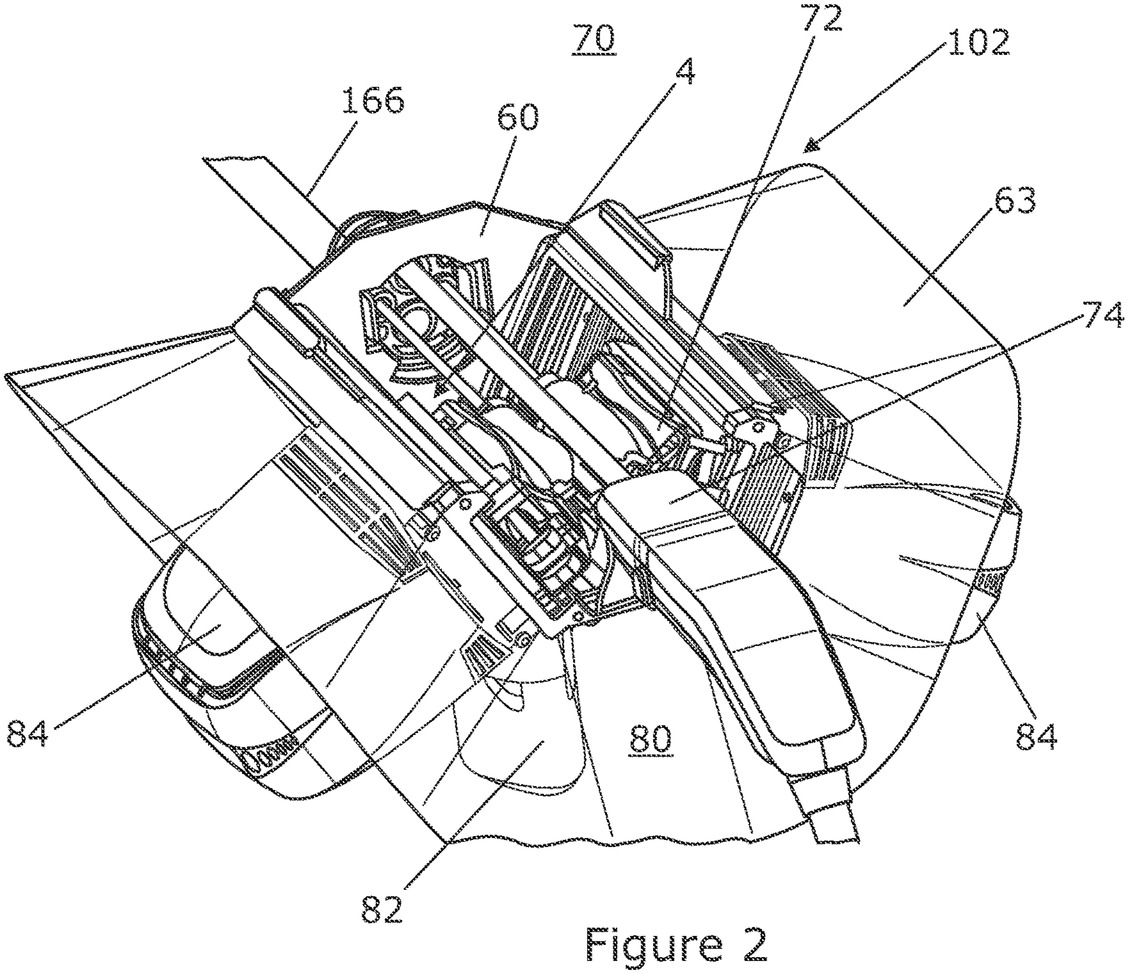
FIG. 2 is a schematic representation of a barrier assembly according to an embodiment of the second aspect of the invention shown in use.

FIG. 2 shows a barrier assembly 102 that is the same as barrier assembly 2 (shown in FIG. 1), except barrier assembly 102 further comprises a port 166, removably attachable to the bracket 60.

The barrier assembly 102 is also shown in use with components of a surgical robot. The surgical robot comprises a number of sterile components including two surgical instruments 72 and an endoscope 74. Each of the sterile components occupy a sterile region 70, which in this example is positioned above the barrier assembly 2. The surgical robot also comprises a number of reusable non-sterile components including a movable platform 82 to which the bracket 60 is mounted and two motor modules 84. Each of the non-sterile components occupy a non-sterile region 80, which in this example is positioned above the barrier assembly 2. The barrier assembly 2 may therefore act as a sterility barrier between the sterile region 70 and the non-sterile region 80.

In use, the drape 63 may extend further than is shown in order to further cover the non-sterile components of the surgical robot. Further, the drape 63 may be sleeve shaped wherein a first end is removably attachable to the bracket 60 (as shown in FIG. 2) and a second end is removably attachable to another portion of the surgical robot, such as a manipulator arm. The drape 63 may thereby encase non-sterile components of the surgical robot to provide a sterility barrier between them and sterile surfaces within a sterile environment such as a surgical operating theatre. The drape 63 may also be flexible to allow adaption of shape with respect to the configuration of the surgical robot.

The port 166 may support the surgical instruments 72 and endoscope 74 and facilitate their insertion into a patient via a natural orifice or incision.

The sterile and non-sterile regions 70 and 80 above and below the barrier assembly 2 described above when the invention is in use are also present in each of the other embodiments shown in FIGS. 1 and 3 to 12.

However, it is to be understood that barrier assemblies, barrier cartridges and barriers according to embodiments of the invention may be configured to act as sterility barriers in the opposite direction as well. For instance, in the embodiment shown in FIG. 2, a sterile region could be defined below the barrier assembly 2 and a non-sterile region could be defined above the barrier assembly 2.

Figure 3:
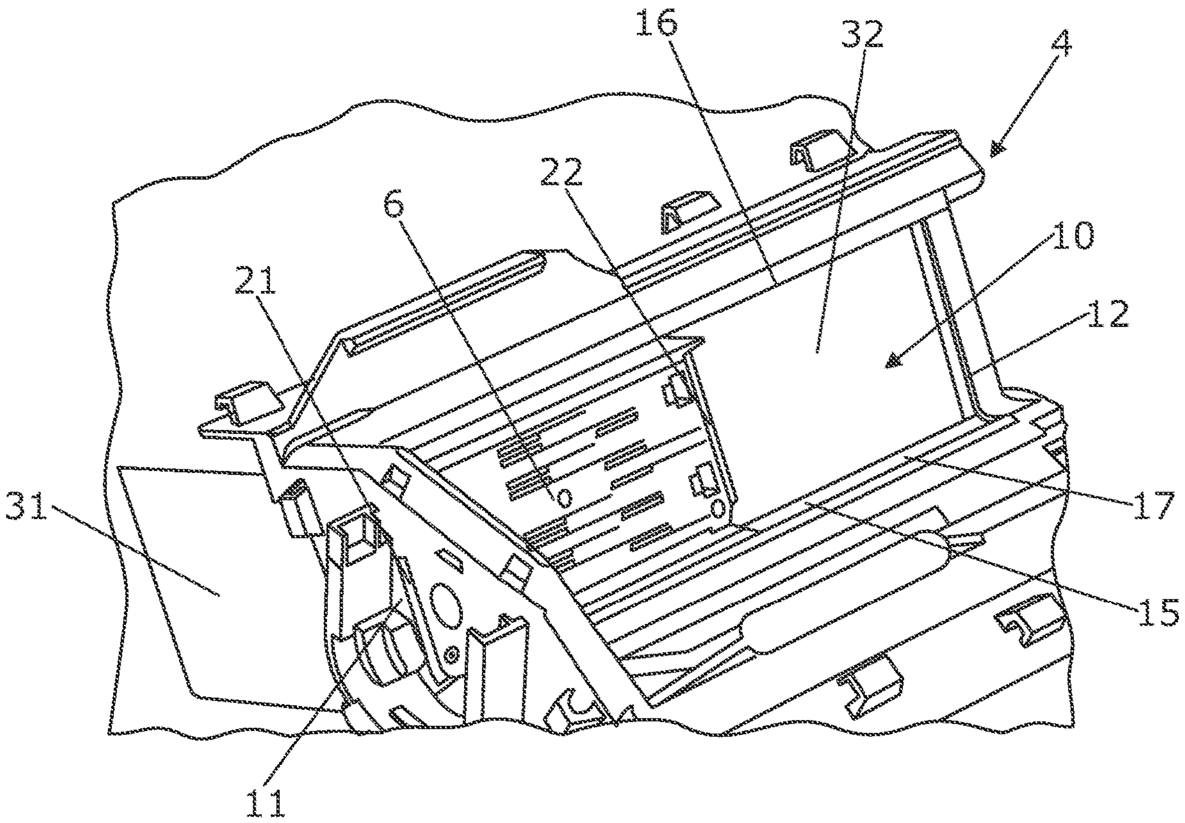
FIG. 3 is a schematic representation of a barrier cartridge according to an embodiment of the first aspect of the invention.

With respect to FIG. 3, one of the barrier cartridges 4 shown in FIG. 1 is described in further detail. However, the other of the barrier cartridges 4 shown in FIG. 1 may be considered as comprising the same features as those described below.

The barrier cartridge 4 further comprises a barrier receiving portion 10, a first flex card 31 and a second flex card 32. The barrier receiving portion 10 comprises a first end 11, a second end 12 spaced apart from the first end 11, a first side 15 and a second side 16 spaced apart from the first side 15. The first and second sides 15, 16 each extend between the first and second ends 11, 12. The barrier 6 is attachable to the barrier receiving portion 10 such that it extends between the first and second sides of the barrier receiving portion 15, 16 and is movable between the first and second ends of the barrier receiving portion 11, 12.

The barrier 4 comprises a first end 21 and a second end 22. The first flex card 31 is operatively connected to the first end of the barrier 21 and the first end of the barrier receiving portion 11. Similarly, the second flex card 32 is operatively connected to the second end of the barrier 22 and the second end of the barrier receiving portion 12.

In this embodiment of the invention, each flex card 31, 32 is attachable to the respective end of the barrier 6 and is slidably receivable by the respective end of the barrier receiving portion 10. Further, each flex card 31, 32 comprises a portion that is positioned internally of the barrier receiving portion 10 and a portion that is positioned externally of the barrier receiving portion 10.

In the example shown in FIG. 3, the barrier 6 is positioned towards the first end 11 of the barrier receiving portion 10. There is therefore little or no gap between the first end of the barrier 21 and the first end of the barrier receiving portion 11 so only a small portion of the first flex card 31 is required to act as a sterility barrier across the gap between the first end of the barrier 21 and the first end of the barrier receiving portion 11. Accordingly, the majority of the first flex card 31 is positioned externally of the barrier receiving portion 10.

Conversely, there is a relatively large gap between the second end of the barrier 22 and the second end of the barrier receiving portion 12 so the majority of the second flex card 31 is required to act as a sterility barrier across the gap between the second end of the barrier 21 and the second end of the barrier receiving portion 11. Accordingly, the majority of the second flex card 31 is positioned internally of the barrier receiving portion 10.

However, as the barrier 6 is movable within the barrier receiving portion 10 (between the first and second ends 11, 12) the configurations of the first and second flex cards 31, 32 may adjust with respect to the position of the barrier 6. For example, as the barrier 6 moves towards the second end of the barrier receiving portion 12 from the position it is shown in FIG. 3, the first and second flex cards 31, 32 will move with it by sliding through the respective ends 11, 12 of the barrier receiving portion 10. Therefore, more of the first flex card 31 will become positioned internally of the barrier receiving portion 10 and more of the second flex card 32 will become positioned externally of the barrier receiving portion 10.

The movement of the flex cards 31 and 32 alongside the barrier 6 ensures that a sterility barrier spans across the entirety of the barrier receiving portion 10, no matter what position the barrier 6 is in.

In this embodiment of the invention, the barrier receiving portion 10 further comprises a first channel 17 extending along the first side 15 and a second channel (not shown) extending along the second side 16. A first side of each flex card is slidably receivable within the first channel 17 and a second side of each flex card is slidably receivable within the second channel (not shown). The first and second channels may support the sides of the flex cards and ensure that they remain in the necessary position to act as a sterility barrier across the barrier receiving portion 10.

Figure 4A:
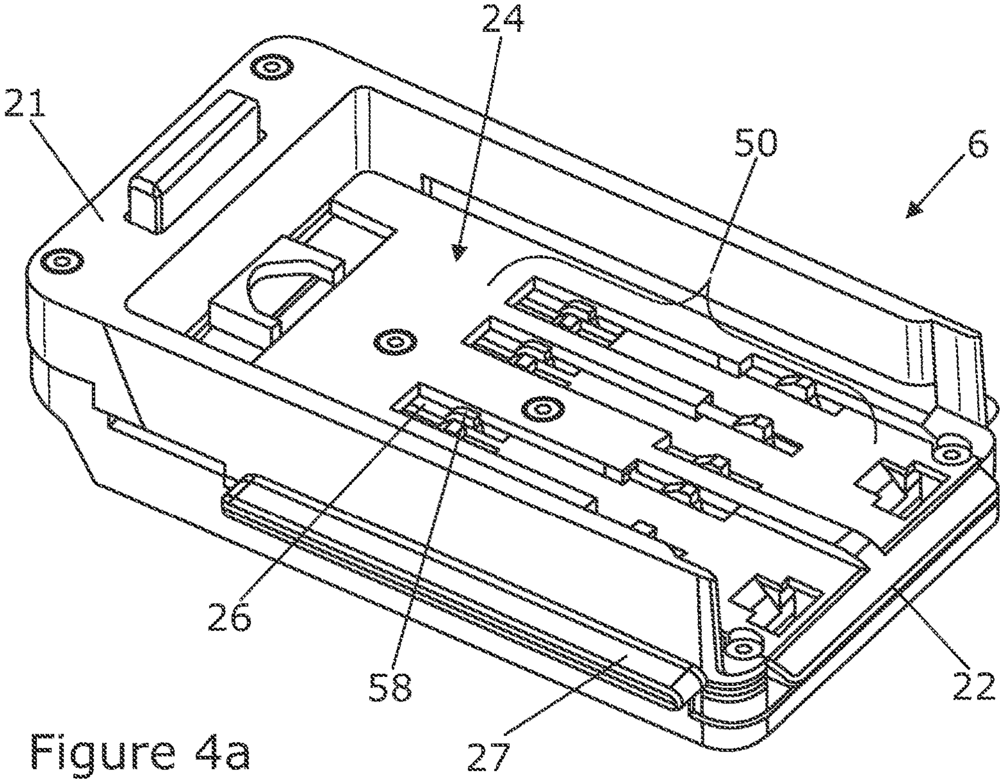
FIGS. 4*a*, 4*b* and 4*c* are schematic representations of a barrier according to an embodiment of the third aspect of the invention, showing a perspective view, a cross-sectional view and a planar view respectively.
Figure 4B:
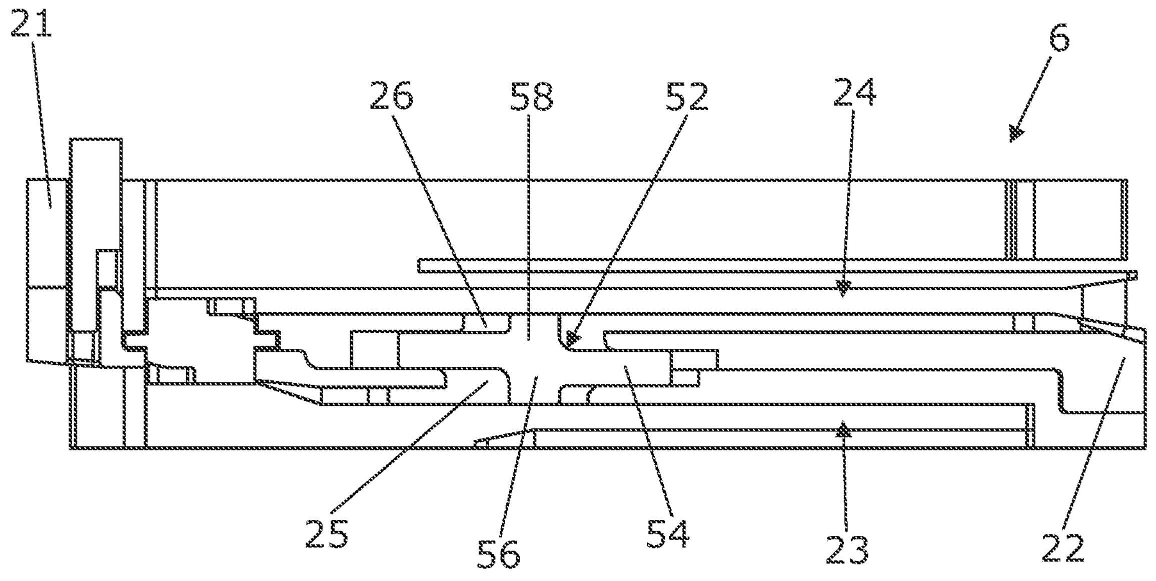
Figure 4C:
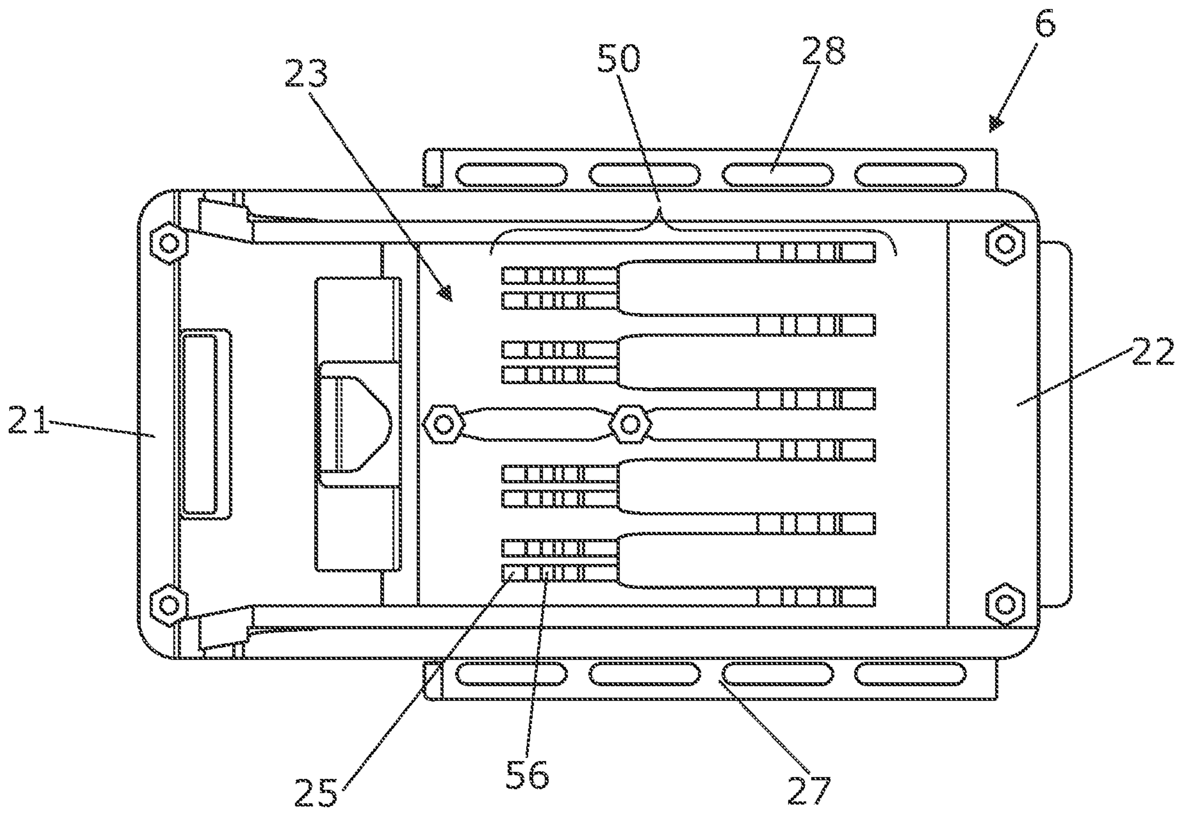

Referring now to FIGS. 4*a*, 4*b* and 4*c*, the barrier 6 further comprises a first cartridge interface 27 slidably engageable with the first channel 17 of the barrier receiving portion 10 (shown in FIG. 3) and a second cartridge interface 28 slidably engageable with the channel of the barrier receiving portion 10. Therefore the first and second channels of the barrier receiving portion 10 may support the sides of the barrier 6 as well as the sides of the first and second flex cards 31, 32. This may help provide a continuous sterility barrier across the barrier receiving portion 10 as the channels promote alignment of the flex cards 31, 32 with the barrier 6.

Still referring to FIGS. 4*a*, 4*b* and 4*c*, the barrier also comprises a first face 23 (see FIG. 4*c*), a second face 24 (see FIG. 4*a*) spaced apart from the first face 23 and a translator mechanism 50 extending between the first face 23 and the second face 24.

The translator mechanism comprises a plurality of translators 52 (see FIG. 4*b*), a plurality of first apertures 25 (see FIG. 4*c*) positioned in the first face 23 and a plurality of second apertures 26 (see FIG. 4*a*) positioned in the second face 24.

Each translator 52 comprises a body 54 positioned between the first face 23 and the second face 24, an actuation portion 56 accessible through a respective one of the first apertures 25, and a translation portion 58 accessible through a respective one of the second apertures 25.

Each actuation portion 56 is movable within the respective first aperture 25 and is also operatively connected to the respective body 54 and to the respective translation portion 58. Therefore, movement of the actuation portion 56 causes corresponding movement of the body 54 in the space between the first and second faces 23, 24 and the translation portion 58 within the respective second aperture 26.

Each body 54 maintains a barrier between the first and second apertures 25, 26 irrespective of its position in the space between the first and second face 23, 24.

In use, the first face 23 may be attachable to a first movable interface (not shown) and the second face 24 may be attachable a second movable interface (not shown). The first movable interface may form part of a non-sterile component such as a motor module and the second movable interface may form part of a sterile component such as a driver module. The barrier 6 therefore acts as a sterility barrier between the first and second movable interfaces.

Further, the first movable interface may comprise a plurality of actuators (not shown), such as motor actuators, which are each engageable with a respective actuation portion 56 and configured to actuate that actuation portion 56 within the respective first aperture 25. The second movable interface may also comprise a plurality of actuators (not shown), each engageable with a respective translation portion 58 and configured to be actuated by the translation portion 58 moving within the respective second aperture 26.

As movement of each actuation portion 56 causes equivalent movement of the body 53 and translation portion 58, each translator 52 may translate movement of an actuator forming part of the first movable interface to movement of an actuator forming part of the second movable interface.

Further, the body 58 of each translator 52 maintains a barrier between the first and second apertures 25, 26 irrespective of its position and therefore acts as a sterility barrier between first (non-sterile) movable interface and the second (sterile) movable interface.

Hence the barrier 6 provides a sterility barrier that allows a non-sterile moving part to interact with a sterile moving part without compromising the sterility of the sterile moving part.

In the example shown in FIGS. 4*a* to 4*c*, the first and second apertures 25, 26 are first and second linear slots respectively (for simplicity, the first and second slots are also designated by the reference numerals 25 and 26 respectively), whereby the respective actuation and translation portions 56, 58 are movable linearly within the first and second linear slots 25, 26 respectively.

Each slot 25, 26 is substantially rectangular in shape and may be defined as having a width and a length. The width of each slot 25, 26 may be configured to prevent movement of the respective actuation or translation portion 56, 58 in a direction parallel to the width. The length of each slot 25, 26 may be configured such that the respective actuation or translation portion 56, 58 is movable linearly along the length. Hence each actuation or translation portion 56, 58 is movable linearly only within the respective slot 25, 26.

In order for the body 54 to maintain a sterility barrier between the first and second slots 25, 26, the body 54 has a width that is at least the approximate width of first and second slots 25, 26. Further the body 54 may extend a first length either side of the translation portion 56 such that the body 54 prevents objects passing through the first slot 25, irrespective of the position of the translation portion 56 within the first slot 25. In this example, the first length is at least the length of the first slot 25 to ensure that a gap is not allowed between the limits of the first slot 25 and the body 54. Similarly, the body 54 may extend a second length either side of the actuation portion 58 such that the body 54 prevents objects passing through the second slot 26, irrespective of the position of the actuation portion 58 within the second slot 26. In this example, the second length is at least the length of the second slot 26 to ensure that a gap is not allowed between the limits of the second slot 26 and the body 54.

Figure 5:
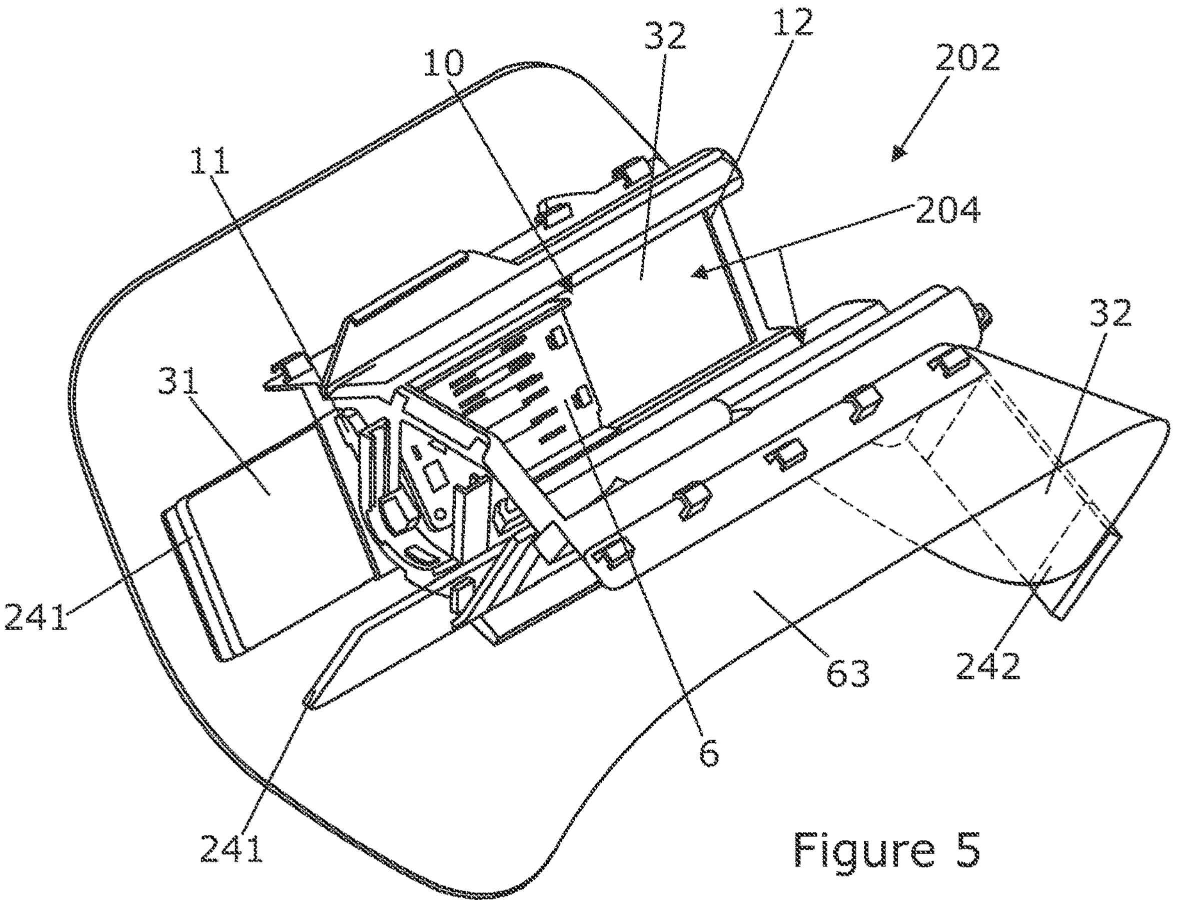
FIG. 5 is a schematic representation of a barrier assembly according to an embodiment of the second aspect of the invention comprising flex card pockets.

FIG. 5 shows a barrier assembly 202 which is similar to the barrier assembly 2 (shown in FIG. 1), except it comprises two barrier cartridges 204 that each further comprise a flex card sterility mechanism 240 comprising a first pocket 241 and a second pocket 242 in addition to the features forming part of the barrier cartridges 4 (shown in FIG. 1). (For ease of reference, features of the barrier assembly 202 that are common with the barrier assembly 2 are given the same reference numeral.)

The first pocket 241 is operatively connectable to the first end 11 of the barrier receiving portion 10 and adapted to receive a portion of the first flex card 31 that is positioned externally of the barrier receiving portion 10. Similarly, the second pocket 242 is operatively connectable to the second end of the barrier receiving portion 12 and adapted to receive a portion of the second flex card 32 that is positioned externally of the barrier receiving portion 10.

Each pocket 241, 242 acts to protect the sterility of the portion of each flex card 31, 32 that is positioned externally of the barrier receiving portion 10, particularly the face of each flex card 31, 32 which is required to remain sterile when in use. In order to achieve this, each pocket 241, 242 may comprise a first internal wall and a second internal wall spaced apart from the first internal wall. When the portion of the respective flex card 31, 32 that is positioned externally of the barrier receiving portion 10 is received by the pocket 241, 242, a first face of the flex card may contact the first internal wall only and a second face may contact the second internal wall only. Therefore the sterile face of the flex card 31, 32 may not be contaminated by contacting the non-sterile first internal wall of the pocket 241, 242.

Figure 6A:
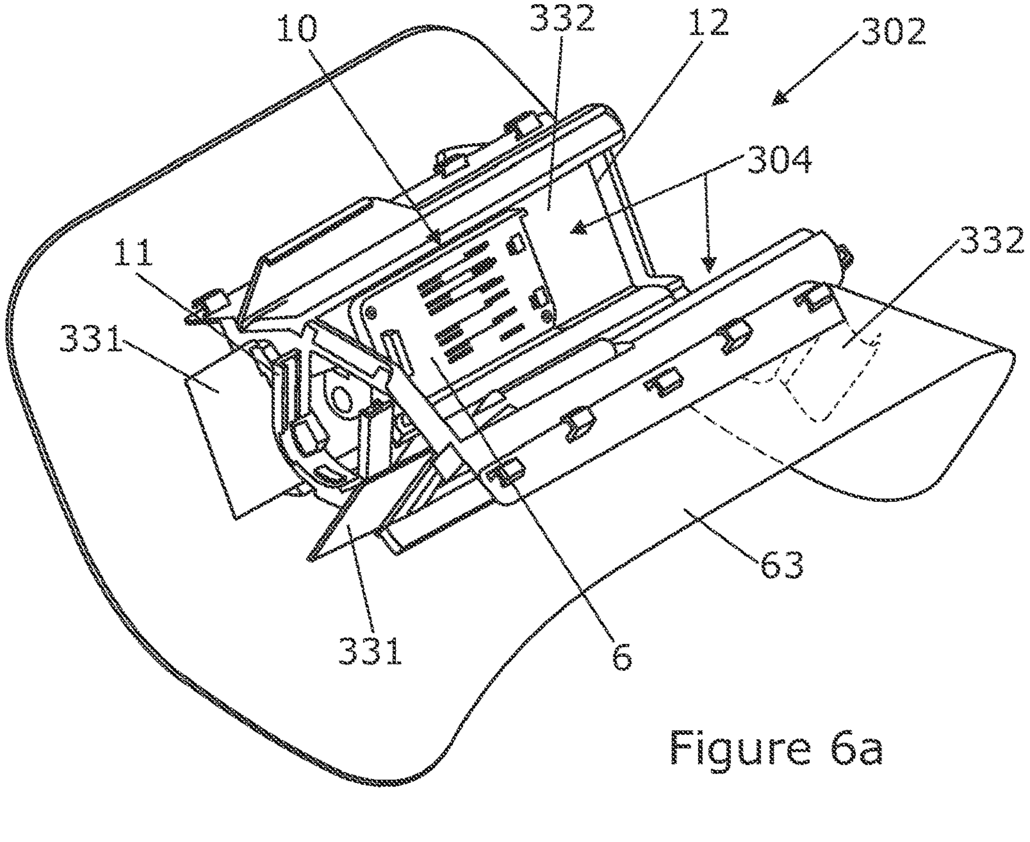
FIGS. 6*a* and 6*b* are schematic representations of a barrier assembly according to an embodiment of the second aspect of the invention comprising rollable/foldable flex cards.
Figure 6B:
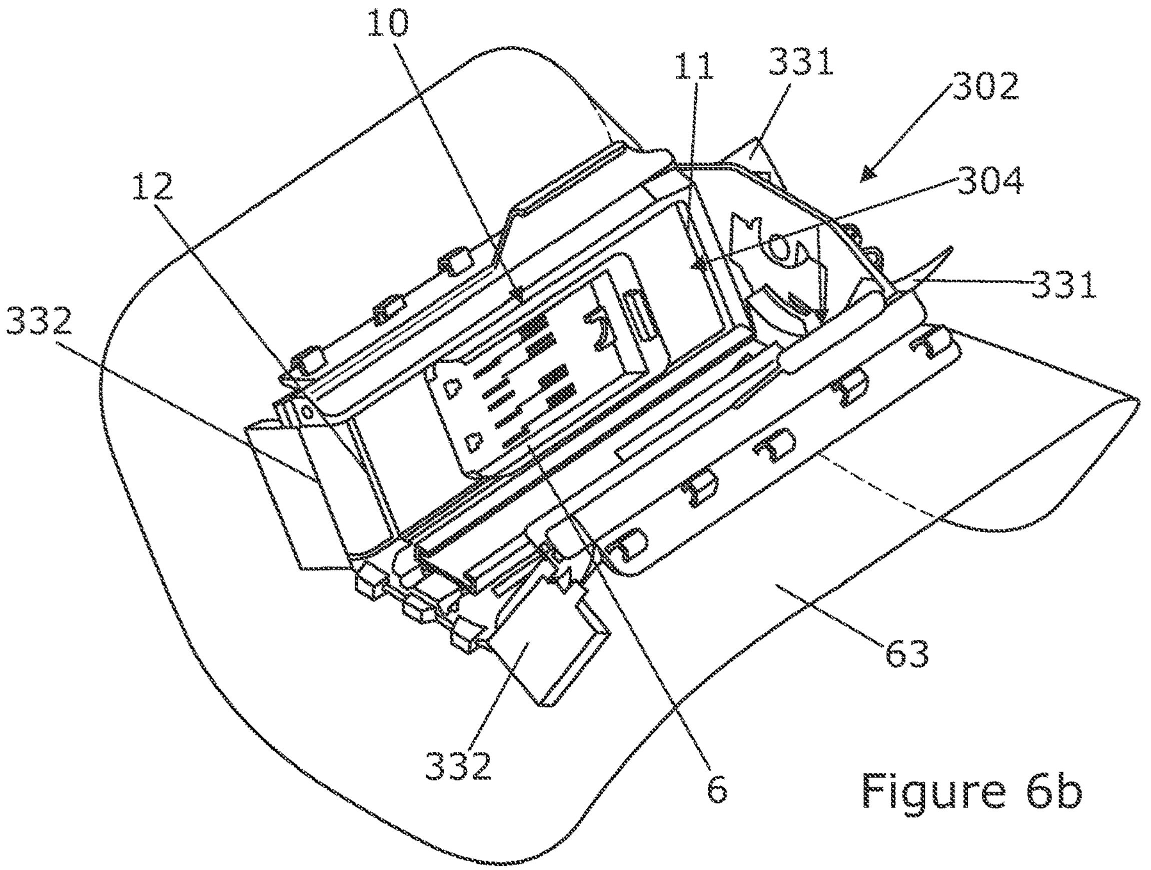

Referring now to FIGS. 6*a* and 6*b*, a barrier assembly 302 is shown which is similar to the barrier assembly 2 (shown in FIG. 1), except it comprises a different flex card sterility mechanism 340. In this embodiment of the invention, the barrier assembly 302 comprises first and second flex cards 331, 332 wherein a portion of each flex card that is positioned externally of the barrier receiving portion is caused to roll or fold back on itself.

Figure 7A:
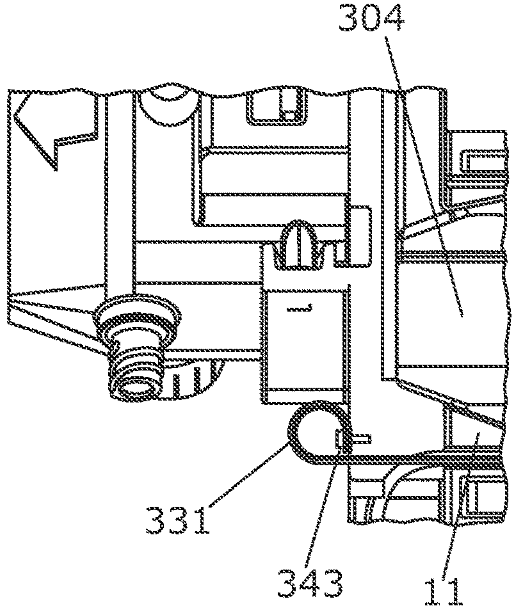
FIGS. 7*a* and 7*b* are schematic representations of a flex card shown in FIGS. 6*a* and 6*b*, the flex card shown in two configurations.
Figure 7B:
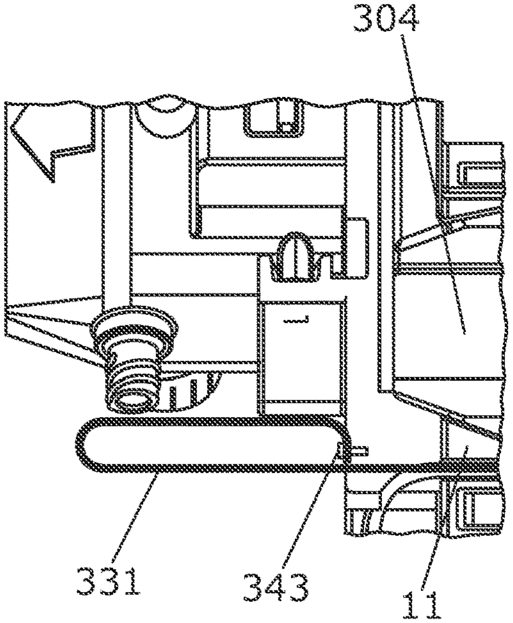

FIGS. 7*a* and 7*b* show a part of a barrier cartridge 304 which forms part of the barrier assembly 302 shown in FIGS. 6*a* and 6*b* and, in particular, show the sterility mechanism. (The barrier cartridge 304 is similar to the barrier cartridge 4 shown in FIG. 3.)

The flex card sterility mechanism 340 comprises a first anchor 343 attachable to the first flex card 331 such that the first flex card 331 extends from the first end of the barrier (not shown) to the first anchor 343 via a first end of the barrier receiving portion 11.

A portion of the first flex card 331 that is positioned internally of the barrier receiving portion (not shown) may extend between the barrier (not shown) and the first end of the barrier receiving portion 11 while a portion of the first flex card 331 that is positioned externally of the barrier receiving portion may extend from first end of the barrier receiving portion 11 to the first anchor 343.

The first anchor 343 is positioned, on the barrier cartridge 304, proximate to the first end of the barrier receiving portion 11 such that the portion of the first flex card 331 that is positioned externally of the barrier receiving portion is caused to roll or fold back on itself in order to attach to the anchor.

FIG. 7*a* shows an example configuration of the barrier cartridge 304 in which the barrier is positioned closely to the second end of the barrier receiving portion such that the majority of the first flex card 331 is positioned internally of the barrier receiving portion to act as a sterility barrier across the gap between the barrier and the first end of the barrier receiving portion. Therefore only a relatively small portion of the first flex card 331 is positioned externally of the barrier receiving portion resulting in a tight roll of the portion of the first flex card 331 that extends between the first end of the barrier receiving portion 11 and the first anchor 343.

However, FIG. 7*b* shows an example configuration of the barrier cartridge 304 in which the barrier is positioned closely to the first end of the barrier receiving portion such that the majority of the first flex card 331 is positioned externally of the barrier receiving portion. This is because only a relatively small portion of the first flex card 331 is required to act as a sterility barrier across the gap between the barrier and the first end of the barrier receiving portion. Therefore, in comparison to FIG. 7*a*, a larger roll is formed by the portion of the first flex card 331 that extends between the first end of the barrier receiving portion 11 and the first anchor 343.

In both FIGS. 7*a* and 7*b*, the first anchor 343 is positioned, on the barrier cartridge 304, such that a first (non-sterile in use) face of the first flex card 331 forms the outer face of the folded/rolled portion of the first flex card 331 that is positioned externally of the barrier receiving portion. Accordingly, a second (sterile) face of the first flex card 331 forms the inner face of the folded/rolled portion of the first flex card that is positioned externally of the barrier receiving portion. The portion of the second face of the first flex card 331 that is positioned externally of the barrier receiving portion is therefore substantially concealed within the fold/roll and protected from contacting a non-sterile surface.

Although the inner face of the folded/rolled portion of the first flex card is protected, the sides of the first flex card remain exposed and could therefore become contaminated. However, these contaminated sides of the first flex card 331 may be slidably received by respective channels, forming part of the barrier receiving portion. The channels may therefore conceal the contaminated sides the flex card when positioned internally of the barrier receiving portion, hence preventing contamination of a sterile region.

Referring back to FIGS. 6*a* and 6*b*, each barrier cartridge 304 may also comprise a second anchor (not shown) that is similarly attachable to the second flex card 332. It is to be understood that the second flex card may therefore be configured equivalently to the first flex card and may benefit from the same advantages.

Referring now to FIGS. 8 to 10*b*, a barrier assembly 402 is shown which is similar to the barrier assembly 2 (shown in FIG. 1), except it comprises a different flex card sterility mechanism 440.

In this embodiment of the invention, the first and second flex cards 431, 432 are attachable to a respective end of the barrier receiving portion 411, 412 rather being slidably received by said end. The flex card sterility mechanism 440 comprises a plurality of fold-lines 439 extending across each flex card substantially perpendicular to the first and second sides of the barrier receiving portion 15, 16 when in use such that each flex card 431, 432 is corrugated and thereby extendible or contractable as the barrier 6 moves between the first end 411 and the second end 412 of the barrier receiving portion. (For ease of reference, features of the barrier assembly 202 that are common with the barrier assembly 2 are given the same reference numeral.)

Due to the corrugation, each flex card 431, 432 is able to extend or contract in length, in an accordion-like fashion, depending on the position of the barrier 6 in the barrier receiving portion 410. Hence there is no requirement for a portion of each flex card 431, 432 to be positioned externally of the barrier receiving portion 410.

Figure 8:
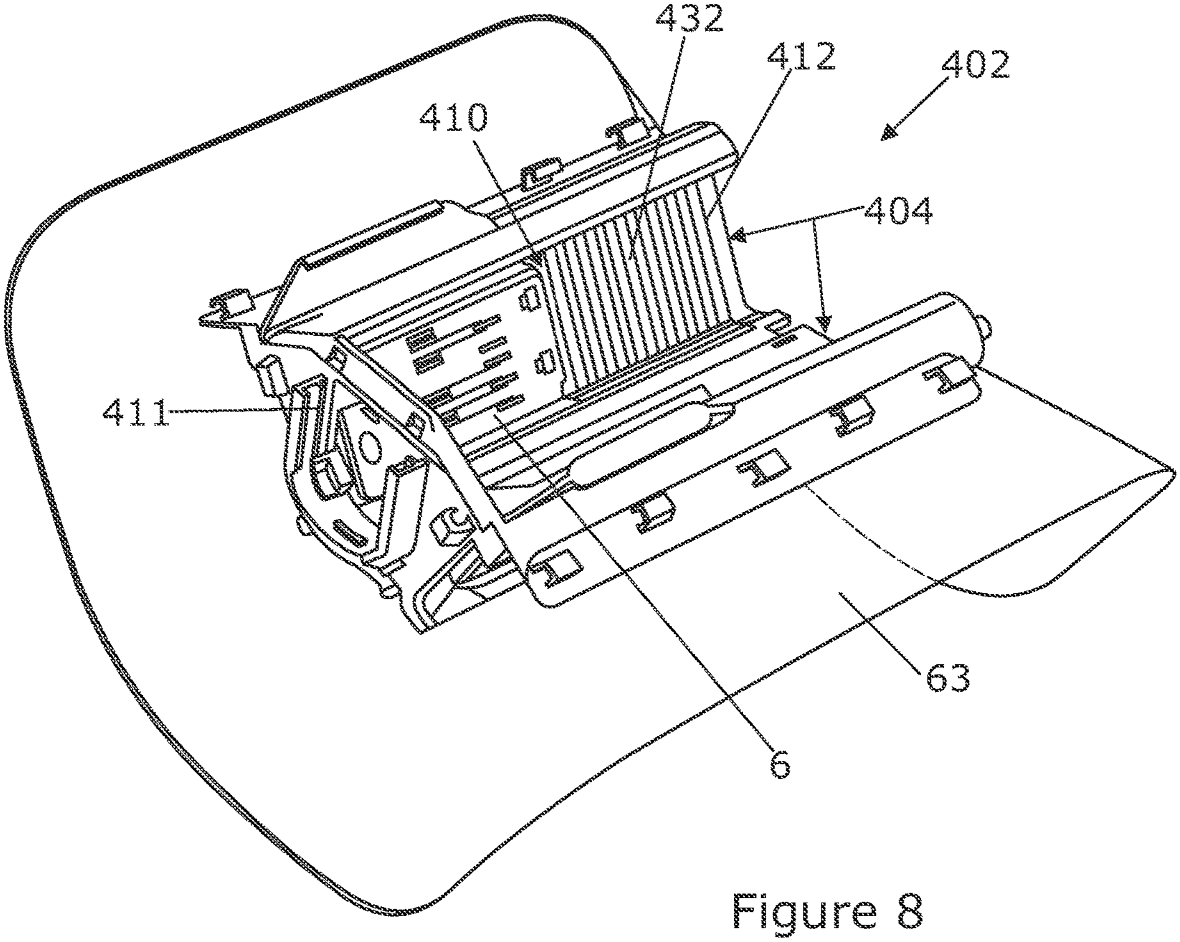
FIG. 8 is a schematic representation of a barrier assembly according to an embodiment of the second aspect of the invention comprising corrugated flex cards.
Figure 9A:
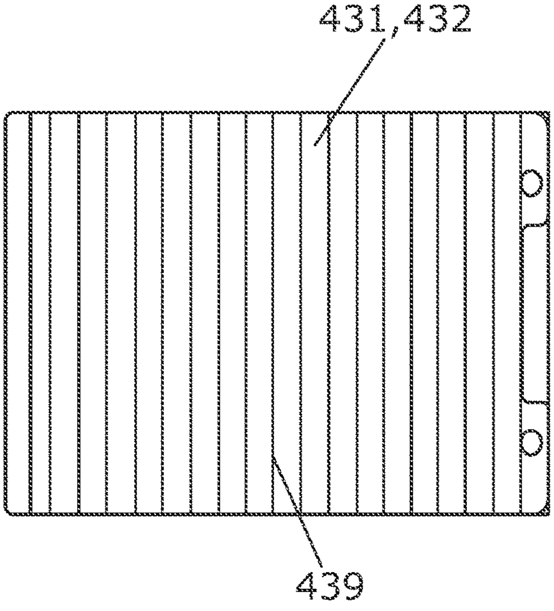
FIGS. 9*a* and 9*b* are schematic representations of a corrugated flex card forming part of a barrier cartridge according to an embodiment of the first aspect of the invention, showing a planar view and a cross-sectional view respectively.
Figure 9B:
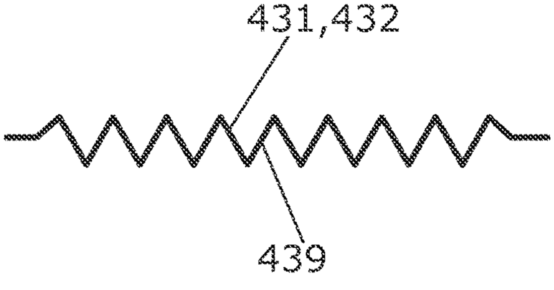

In FIG. 8, an example of the embodiment of the invention is shown in which the barrier 6 is positioned at the first end of the barrier receiving portion 411. Therefore the first flex card (not shown) is fully contracted between the first end of the barrier receiving portion 411 and the barrier 6. Meanwhile, the second flex card 432 is extended across the gap between the barrier 6 and the second end of the barrier receiving portion 412 to act as a sterility barrier.

Figure 10A:
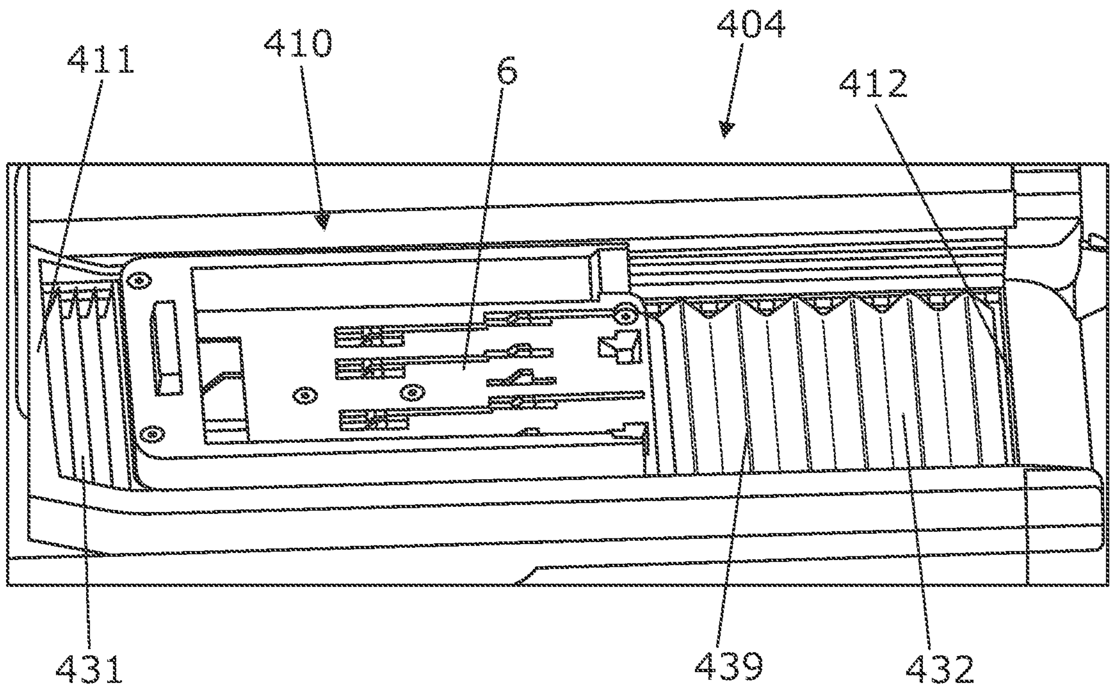
FIGS. 10*a* and 10*b* are schematic representations of a barrier cartridge according to an embodiment of the first aspect of the invention comprising corrugated flex cards, showing the barrier cartridge in two configurations.
Figure 10B:
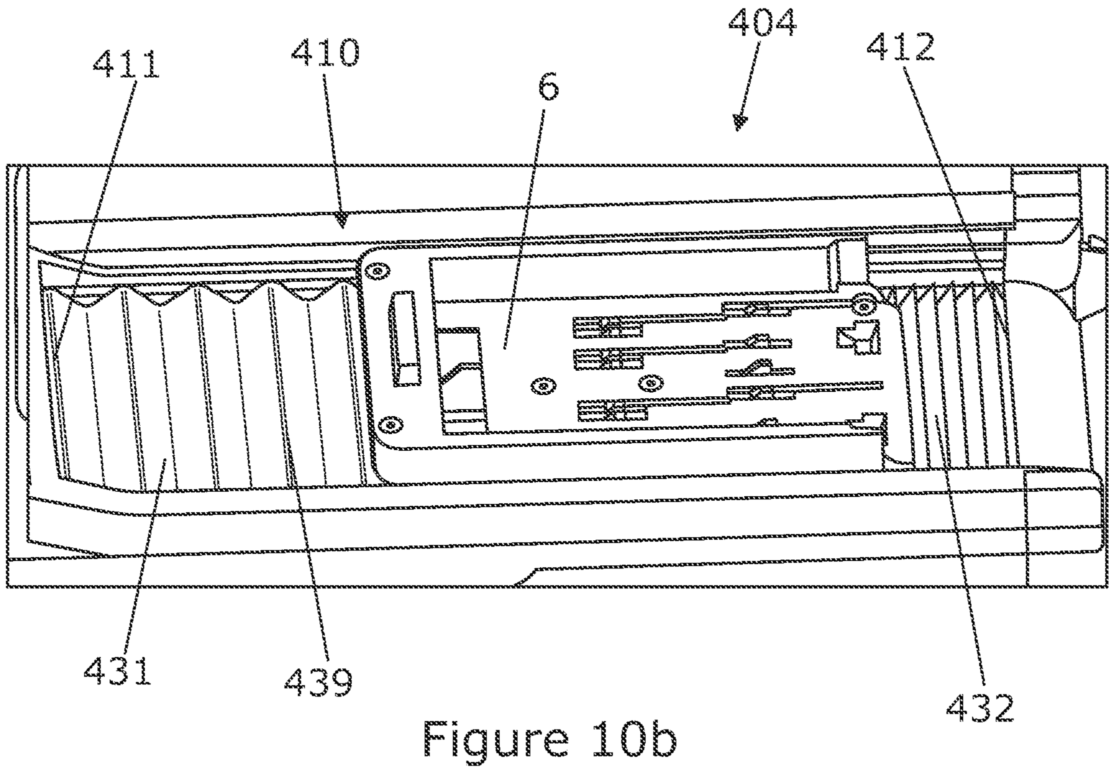

In FIGS. 10*a* and 10*b*, a further example of this embodiment of the invention, particularly a barrier cartridge 404, is shown in two configurations. The configuration shown in FIG. 10*a* closely resembles the configuration shown in FIG. 8, wherein the barrier 6 is positioned towards the first end of the barrier receiving portion 411, the first flex card 431 is substantially contracted and the second flex card 432 is substantially extended.

FIG. 10*b* shows a configuration that demonstrates how each flex card 431, 432 changes when the barrier 6 is moved towards the second end of the barrier receiving portion 412. As the gap between the barrier 6 and the second end of the barrier receiving portion 412 reduces, the second flex card 432 contracts by increasingly folding against itself along the fold lines 439. Simultaneously, the gap between the barrier 6 and the first end of the barrier receiving portion 411 increases, therefore the first flex card 431 extends by unfolding and flattening in order to stretch across the increasing gap.

The result is that the combination of the barrier 6 and the flex cards 431, 432 provides a sterility barrier across the barrier receiving portion 410, irrespective of where the barrier 6 is positioned.

Figure 11A:
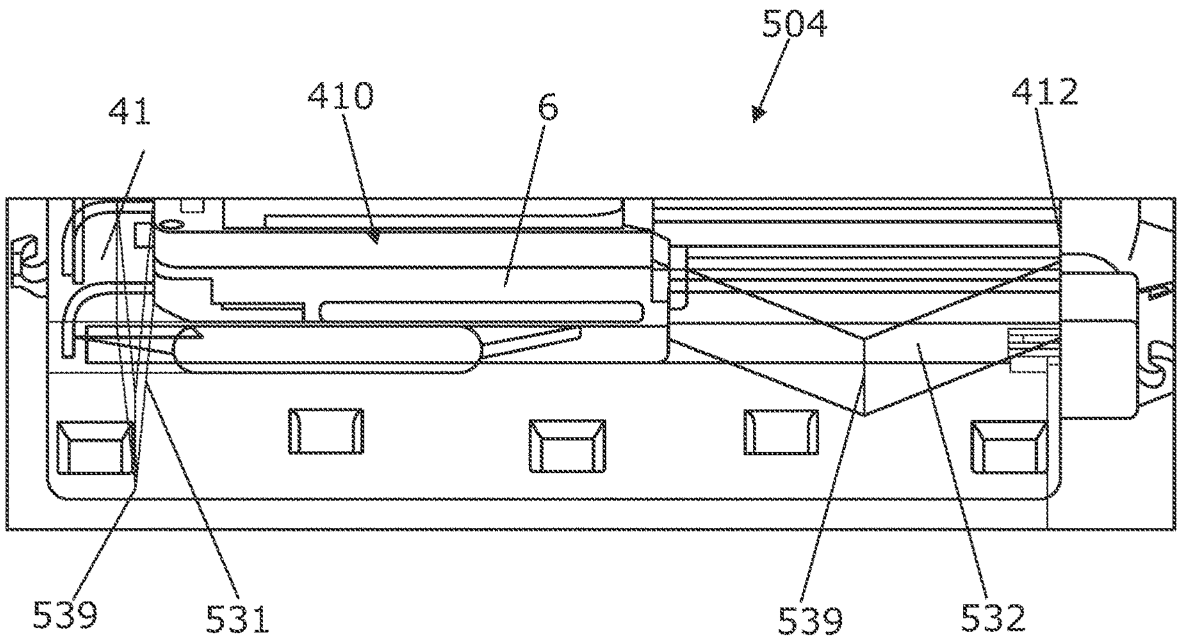
FIGS. 11*a* and 11*b* are schematic representations of a barrier cartridge according to an embodiment of the first aspect of the invention comprising corrugated flex cards with a single fold-line, showing the barrier cartridge in two configurations.
Figure 11B:
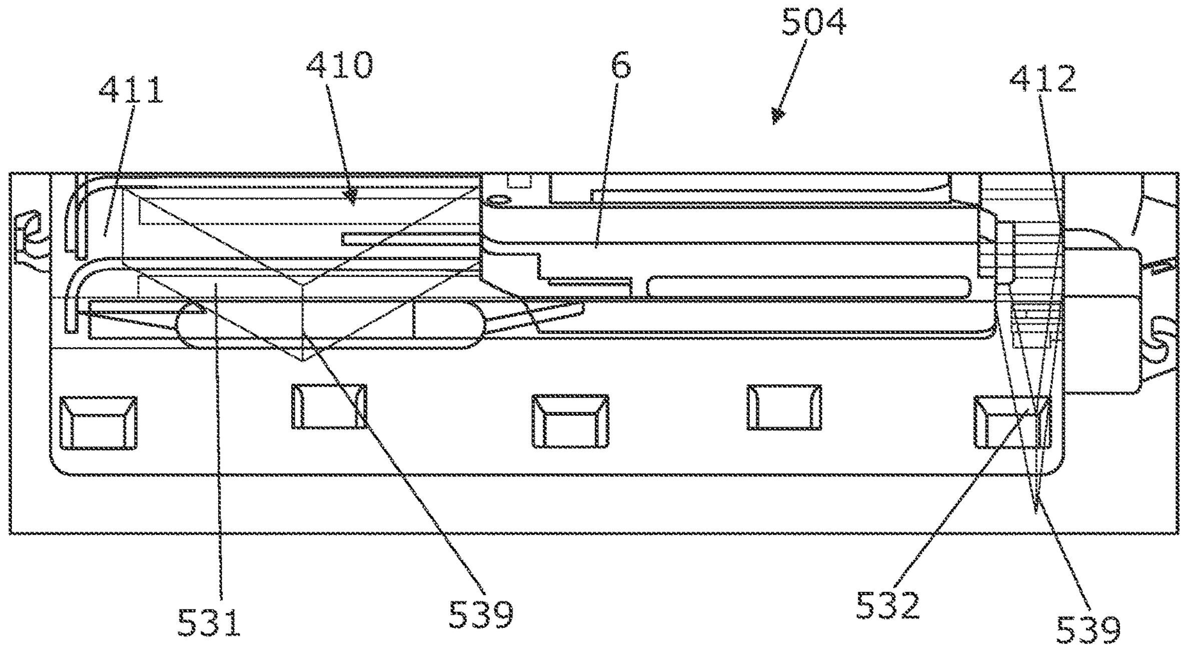

Referring now to FIGS. 11*a* and 11*b*, a barrier cartridge 504 is shown which is similar to the barrier cartridge 404 (shown in FIGS. 10*a* and 10*b*), except it comprises a different flex card sterility mechanism 540 which comprises a single fold-line 539 only extending across each flex card 531, 532. (For ease of reference, features of the barrier assembly 202 that are common with the barrier assembly 2 are given the same reference numeral.)

In this example, the fold-line 539 is positioned approximately in the middle of each flex card 531, 532 to allow the flex card 531, 532 to substantially fold in half when required to fully contact due to the gap between the barrier 6 and the respective end of the barrier receiving portion 411, 412 being minimised.

FIG. 11*a* shows a first configuration of this embodiment of the invention, in which the barrier 6 is positioned closely to the first end of the barrier receiving portion 411. The first flex card 531 is substantially folded against itself along the fold-line 539 in order for the ends of first flex card 531 to contract together within the small gap between the barrier 6 and first end of the barrier receiving portion 411. Conversely, the second flex card 532 is substantially unfolded in order to span the larger gap between the barrier 4 and the second end of the barrier receiving portion 412.

FIG. 11*b* shows a second configuration that demonstrates how each flex card 531, 532 changes when the barrier 6 is moved towards the second end of the barrier receiving portion 412. The configuration of the flex cards 531, 532 essentially reverses whereby the first flex card 531 unfolds in order to stretch across the increased gap between the barrier 6 and the first end of the barrier receiving portion 411. Meanwhile the second flex card 532 substantially folds against itself along the fold-line 539 in order that the ends of the flex card contract together in the reduced gap between the barrier 6 and the second end of the barrier receiving portion 412.

Although each flex card comprises only one fold-line, the result is still that the combination of the barrier 6 and the flex cards 531, 532 provides a sterility barrier across the barrier receiving portion 410, irrespective of where the barrier 6 is positioned.

Further, the flex cards 531, 532 may be configured to fold in a particular direction. In order to reduce the likelihood of contaminating the sterile region (which is above the barrier cartridge 504 in this example), each flex card 531, 532 may fold such that the fold-line 539 moves in the direction of the non-sterile region (which is below the barrier cartridge in this example). This prevents a first (non-sterile in use) face of either flex card 531, 532 from moving into the sterile region. Also, as either flex card 531, 532 folds against itself, the second (sterile) face of the flex card becomes increasingly concealed within the fold, the further that the fold-line moves into the non-sterile region. Therefore, the second (sterile) face of the flex card is protected from being contaminated and prevented from introducing contamination into the sterile region.

Figure 12:
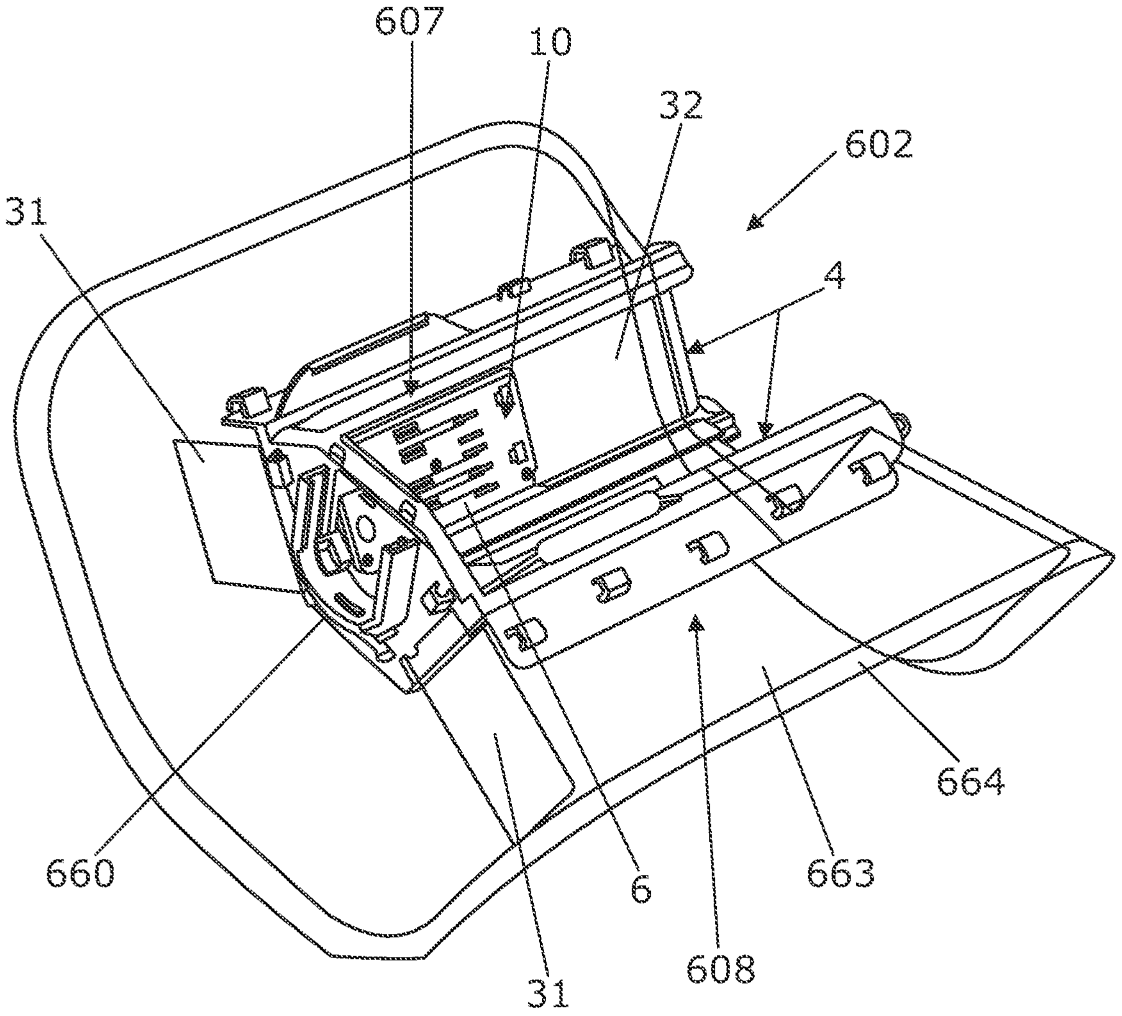
FIG. 12 is a schematic representation of a barrier assembly according to an embodiment of the first aspect of the invention comprising first and second drapes.

Referring now to FIG. 12, a barrier assembly 602 according to an embodiment of the second aspect of the invention is shown which is similar to the barrier assembly 2 (shown in FIG. 1), except it comprises a bracket 660 to which a first drape 663 and a second drape 664 are both removably attachable.

The first drape 663 is operatively connectable to a first face of the bracket 607 (in this example, the first face 607 may be considered as the top face) and the second drape 664 is operatively connectable to a second face of the bracket 608 (in this example, the second face 608 may be considered as the bottom face).

In use, the first face of bracket 607 may be exposed to a sterile region and the second face of the bracket 608 may be exposed to a non-sterile region wherein the barrier assembly 602 acts as a sterility barrier between the sterile and non-sterile regions. (In other embodiments of the invention, the sterile and non-sterile regions may be oppositely configured, and the barrier assembly may still act as a sterility barrier between them.)

Therefore an outer face of the first drape 663 may also be exposed to a non-sterile region, and therefore become non-sterile in use, while the outer face of the second drape 664 may remain sterile in use. Further, a second sterile region may be provided between the first and second drapes 663, 664 (between the inner face of each drape).

The first and second flex cards 31, 32 forming part of each barrier cartridge 4 may be configured such that a portion of each flex card 31, 32 which is positioned externally of the barrier receiving portion 10 is also positioned between the first and second drapes 663, 664. (In the example shown in FIG. 12, the barriers 6 are positioned such that the majority of each first flex card 31 is positioned externally of the barrier receiving portion 10.)

This may prevent a first (non-sterile in use) face of each flex card 31, 32 from entering, and potentially contaminating, the sterile region. It may also protect the second (sterile) face of each flex card 31, 32 from being contaminated due to entering the non-sterile region.

Further, this configuration may protect the outer face of the second drape 664 from being contaminated by contact with the first (non-sterile in use) face of any of the flex cards 31, 32.

The second drape 664 may also provide a level of redundancy to the sterility barrier so that the sterility of sterile surfaces is not compromised if the first drape 663 is damaged.

Although not shown in the figures, each drape 663, 664 may be sleeve-shaped and comprise an end removably attachable to a portion of the surgical robot as well as an end removably attachable to the bracket (as shown in FIG. 12). A non-sterile portion of the surgical robot may therefore be wrapped/encased in each drape 663, 664 to prevent sterile surfaces from contacting the non-sterile surfaces forming part of the surgical robot and thereby becoming contaminated.

Preferences and options for a given aspect, feature or parameter of the invention should, unless the context indicates otherwise, be regarded as having been disclosed in combination with any and all preferences and options for all other aspects, features and parameters of the invention. For example, the corrugated flex cards 431, 432 shown in FIGS. 8 to 10*b* may be used in combination with first and second drapes 663, 664 shown in FIG. 12.

The invention claimed is:

1. A barrier cartridge for providing a sterility barrier between movable interfaces comprising:

a barrier comprising a first end and a second end;

a barrier receiving portion, adapted to receive the barrier, and comprising a first end and a second end spaced apart from one another, a first side and a second side spaced apart from one another and extending between the first and second ends, wherein the barrier is attachable to the barrier receiving portion such that it extends between the first side and the second side of the barrier receiving portion and is movable between the first end and the second end of the barrier receiving portion;

a first flex card operatively connected to both the first end of the barrier and the first end of the barrier receiving portion and extendible between the first and second sides of the barrier receiving portion;

a second flex card operatively connected to both the second end of the barrier and the second end of the barrier receiving portion and extendible between the first side and the second side of the barrier receiving portion; and a flex card sterility mechanism.

2. The barrier cartridge according to claim 1 wherein the flex card sterility mechanism comprises a first pocket operatively connectable to the first end of the barrier receiving portion and adapted to receive a portion of the first flex card that is positioned externally of the barrier receiving portion and a second pocket operatively connectable to the second end of the barrier receiving portion and adapted to receive a portion of the second flex card that is positioned externally of the barrier receiving portion.

3. The barrier cartridge according to claim 1 wherein the flex card sterility mechanism comprises:

a first anchor wherein the first flex card is attachable to the first anchor such that the first flex card extends from the first end of the barrier to the first anchor via the first end of the barrier receiving portion, and a second anchor wherein the second flex card is attachable to the second anchor such that the second flex card extends from the second end of the barrier to the second anchor via the second end of the barrier receiving portion.

4. The barrier cartridge according to claim 1 wherein each flex card is attachable to the respective end of the barrier receiving portion and the flex card sterility mechanism comprises at least one fold-line extending across each flex card substantially perpendicular to the first and second sides of the barrier receiving portion when in use such that each flex card is corrugated and thereby extendible or contractable as the barrier moves between the first end and the second end of the barrier receiving portion.

5. The barrier cartridge according to claim 1 wherein the barrier receiving portion comprises:

a first channel extending along the first side and configured to slidably receive a first side of each flex card, and a second channel extending along the second side and configured to slidably receive a second side of each flex card.

6. The barrier cartridge according to claim 5 wherein the barrier comprises a first cartridge interface slidably engageable with the first channel, and a second cartridge interface slidably engageable with the second channel.

7. A barrier cartridge for providing a sterility barrier between movable interfaces comprising:

a barrier comprising a first end and a second end;

a barrier receiving portion, adapted to receive the barrier, and comprising a first end and a second end spaced apart from one another, a first side and a second side spaced apart from one another and extending between the first and second ends, wherein the barrier is attachable to the barrier receiving portion such that it extends between the first side and the second side of the barrier receiving portion and is movable between the first end and the second end of the barrier receiving portion;

a first flex card operatively connected to both the first end of the barrier and the first end of the barrier receiving portion and extendible between the first and second sides of the barrier receiving portion; and a second flex card operatively connected to both the second end of the barrier and the second end of the barrier receiving portion and extendible between the first side and the second side of the barrier receiving portion, wherein the barrier comprises a first face, a second face spaced apart from the first face and a translator mechanism extending between the first face and the second face, the translator mechanism comprising a plurality of translators wherein each translator comprises:

a body positioned between the first face and the second face, an actuation portion accessible through a first aperture in the first face and moveable within the first aperture, and a translation portion accessible through a second aperture in the second face and moveable within the second aperture, wherein the actuation portion is operatively connected to the body and to the translation portion such that movement of the actuation portion causes movement of the body and the translation portion, and the body maintains a sterility barrier between the first and second apertures irrespective of its position.

8. The barrier cartridge according to claim 7 wherein the first and second apertures of the barrier are first and second linear slots respectively, whereby the respective actuation and translation portions are movable linearly within the first and second linear slots respectively.

9. The barrier cartridge according to claim 7 wherein the first face of the barrier is removably engageable with a motor module comprising a plurality of motor actuators, and the actuation portion of each translator is engageable with a respective one of the motor actuators.

10. The barrier cartridge according to claim 7 wherein the second face of the barrier is engageable with a driver module comprising a plurality of drive actuators, and the translation portion of each translator is engageable with a respective one of the drive actuators.

11. The barrier assembly for providing a sterility barrier between sterile and non-sterile surfaces wherein the barrier assembly is mountable to a platform for a robotic surgical platform and comprises:

a bracket comprising at least one barrier cartridge, the at least one barrier cartridge including:

a barrier comprising a first end and a second end;

a barrier receiving portion, adapted to receive the barrier, and comprising a first end and a second end spaced apart from one another, a first side and a second side spaced apart from one another and extending between the first and second ends, wherein the barrier is attachable to the barrier receiving portion such that it extends between the first side and the second side of the barrier receiving portion and is movable between the first end and the second end of the barrier receiving portion;

a first flex card operatively connected to both the first end of the barrier and the first end of the barrier receiving portion and extendible between the first and second sides of the barrier receiving portion;

a second flex card operatively connected to both the second end of the barrier and the second end of the barrier receiving portion and extendible between the first side and the second side of the barrier receiving portion; and a first drape removably attachable to the bracket.

12. The barrier assembly according to claim 11 wherein the bracket comprises two barrier cartridges.

13. The barrier assembly according to claim 12 further comprising a port removably attachable to the bracket.

14. The barrier assembly according to claim 11 wherein a first face of the bracket is mountable, via the platform, to a manipulator arm configured to movably mount the bracket to a surface and selectively provide the bracket with six degrees of freedom of movement relative to the surface.

15. The barrier assembly according to claim 14 wherein the first drape is sleeve-shaped and comprises a first end removably attachable to the bracket and a second end removably attachable to the manipulator arm such that the first face of the bracket is covered by at least the first drape.

16. The barrier assembly according to claim 11 further comprising a second drape removably attachable to the bracket wherein the first drape is operatively connectable to a first face of the bracket and the second drape is operatively connectable to a second face of the bracket.

* * * * *